(12) United States Patent
Chapeau et al.

(10) Patent No.: US 7,883,902 B2
(45) Date of Patent: Feb. 8, 2011

(54) METHOD AND DEVICE FOR DISPENSING DRY POWDERS

(75) Inventors: Vincent Chapeau, Seraing (BE); Christian Godino, Liège (BE)

(73) Assignees: Occhio, Liege (BE); Logistique Spatiale Wallonne-Wallonia Space Logistics, Liege/Angleur (BE)

(*) Notice: Subject to any disclaimer, the term of this patent is extended or adjusted under 35 U.S.C. 154(b) by 955 days.

(21) Appl. No.: 11/570,161

(22) PCT Filed: Jun. 7, 2005

(86) PCT No.: PCT/EP2005/052612
§ 371 (c)(1),
(2), (4) Date: Dec. 7, 2006

(87) PCT Pub. No.: WO2005/124311
PCT Pub. Date: Dec. 29, 2005

(65) Prior Publication Data
US 2008/0261325 A1    Oct. 23, 2008

(30) Foreign Application Priority Data
Jun. 8, 2004   (BE) .................................. 2004/0282

(51) Int. Cl.
*G01N 1/00*    (2006.01)

(52) U.S. Cl. .................. 436/174; 436/56; 422/63; 422/99; 422/101; 118/50; 118/309

(58) Field of Classification Search ............... 422/63, 422/99, 101; 436/56, 174; 118/50, 309
See application file for complete search history.

(56) References Cited

U.S. PATENT DOCUMENTS

| | | | |
|---|---|---|---|
| 3,472,202 A | 10/1969 | Todd | |
| 4,868,128 A | 9/1989 | Sommer et al. | |
| 5,875,776 A * | 3/1999 | Vaghefi | 128/203.15 |
| 6,209,538 B1 * | 4/2001 | Casper et al. | 128/203.15 |
| 2002/0127701 A1 | 9/2002 | Duncan | |

FOREIGN PATENT DOCUMENTS

| | | |
|---|---|---|
| JP | 2001-242062 | 9/2001 |
| WO | 03074154 A1 | 9/2003 |

* cited by examiner

*Primary Examiner*—Lyle A Alexander
*Assistant Examiner*—Dennis M White
(74) *Attorney, Agent, or Firm*—McCracken & Frank LLP

(57) ABSTRACT

The inventive method for dispersing a dry powder sample in a dispersion chamber consists in vacuuming the chamber with respect to the environment, in dispersing a dry powder in the chamber, by means of a suction generated by the rupture of a membrane which is torn.

4 Claims, 1 Drawing Sheet

METHOD AND DEVICE FOR DISPENSING DRY POWDERS

FIELD OF THE INVENTION

The present invention relates to a method and device for dispersing a sample of dry powder in a dispersion chamber.

BACKGROUND OF THE INVENTION

There is known, for example through the U.S. Pat. No. 4,868,128, a method of dispersing a sample of dry powder in a dispersion chamber comprising:
sealed closure of the said dispersion chamber,
the placing of the sample in means of introducing dry powder into the dispersion chamber,
putting the chamber under negative pressure with respect to a surrounding environment,
dispersion of the dry powder in the chamber by suction thereof inside.

In addition, the device described in the above mentioned patent comprises:
a dispersion chamber connected to a negative-pressure source and situated in a surrounding environment,
means of opening and/or sealed closure of the said dispersion chamber, and
means of introducing the sample of dry powder into the said dispersion chamber.

Unfortunately, this method and this device cause an ordered dispersion of the grains constituting the dry powder because of the existence of a flow and this involves segregation within the dispersed granular materials, preventing a certain homogeneity of dispersion of the grains on a surface.

BRIEF SUMMARY OF THE INVENTION

The aim of the invention is to mitigate the drawbacks of the prior art by procuring an invention making it possible to avoid this segregation and permitting homogeneous, preferably single-layer, distribution of the grains dispersed on the surface.

To resolve this problem, there is provided according to the invention a method as indicated at the start, also comprising
explosion of a membrane that ruptures, this membrane serving as the above mentioned introduction means and being interposed between the said surrounding environment and the interior of the said dispersion chamber,
entry of a fluid composing the surrounding environment through the ruptured membrane, and
entrainment by this fluid of the dry powder placed on the membrane, inside the dispersion chamber in an evenly dispersed manner.

Other embodiments of the method according to the invention are indicated in the accompanying claims.

Another object of the invention is a device as indicated at the start for implementing the method described above.

This device is characterised in that the introduction means comprise a membrane that is interposed between the said surrounding environment and the inside of the said dispersion chamber and on which the sample is disposed, the said membrane being arranged to rupture at a predetermined pressure difference between the said surrounding environment and the said inside of the dispersion chamber.

Other embodiments of the device according to the invention are indicated in the accompanying claims.

Other characteristics, details and advantages of the invention will emerge from the description given below, non-limitingly and making reference to the accompanying drawing.

DETAILED DESCRIPTION OF THE INVENTION

Figure 1:
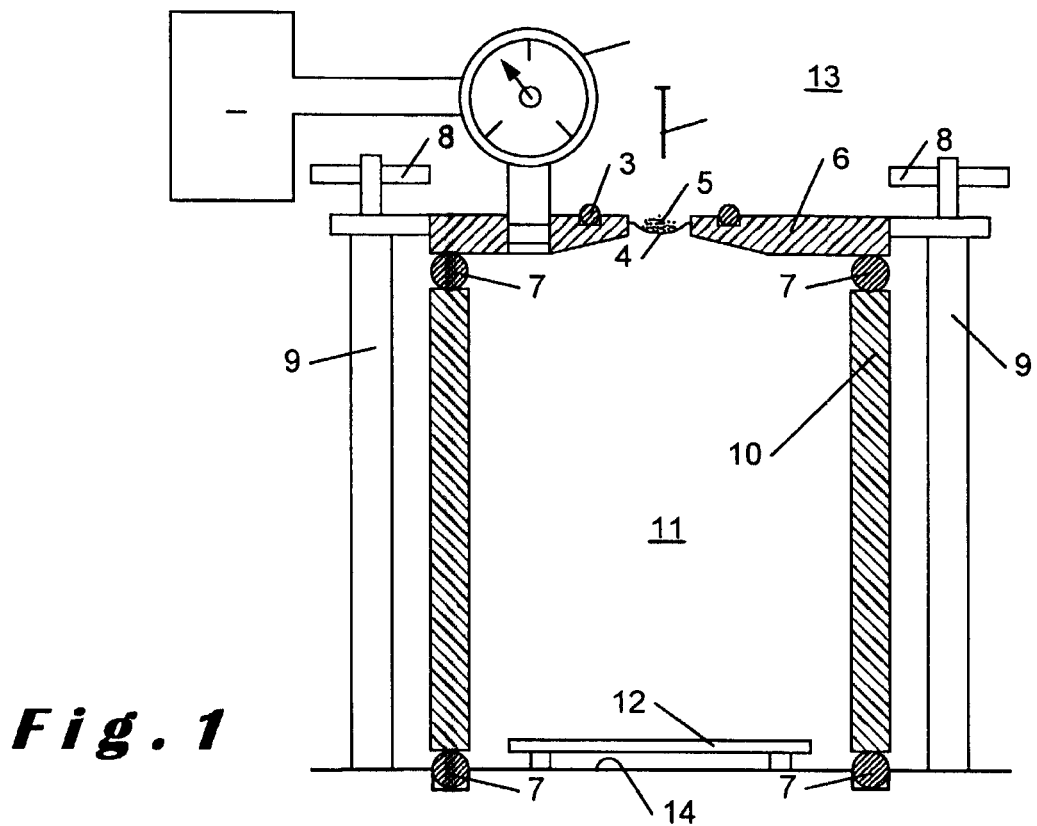
FIG. 1 is a schematic view of a particular embodiment of the device according to the invention.

FIG. 1 illustrates a particular embodiment of the device comprising a vacuum pump 1, a pressure gauge 2, means of introducing a sample into the dispersion chamber 11, in the form of a sample support membrane 4, on which provision is made for disposing a sample of dry powder 5, and a surface (surface to be treated 12) on which the sample of dry powder is to be dispersed. The dispersion chamber 11 consists of a cylinder 10, a top cover 6 and a bottom 14. These elements 10, 6 and 14 can be assembled in order to form a dispersion chamber. On the bottom 14, a seal 7 is placed on which the cylinder 10 must be placed for assembly. Above the cylinder 10, provision is made for placing another seal 7 before closing the dispersion chamber by means of the cover 6. In addition, clamping means, for example of the type with closure column 9 and butterflies 8, ensure a seal by pushing the cover 6 and bottom 1 onto the seals on each side of the cylinder 11. The clamping means 8 and 9 and sealing means 7 therefore form the opening and/or sealed closure means of the device according to the invention. In addition, when the partial vacuum is produced, the cover 6 and bottom 14 exert an even greater pressure on the seals. The cover 6 and bottom 14 therefore grip the cylinder 10 sealingly.

The device that is described above is an apparatus for dispersing a sample of dry powder 5 by explosion in a vacuum dispersion chamber 11. This technique allows the dispersion of micrometric or nanometric grains of dry powder 5 on a surface positioned in the bottom of the dispersion chamber 11, the surface to be treated 12.

This dispersion is carried out by separating and setting in movement the sample of dry powder 5 without producing an ordered movement of the grains making up the dry powder 5, in the dispersion chamber 11. This condition of not generating an ordered movement of the material (a flow) is essential since a flow generates segregation within the dispersed granular materials, which is very detrimental in the context of the subsequent analyses.

In order to perform the dispersion operation, a low-intensity explosion is generated. This explosion is generated by the rupture of the sample-holding membrane 4, the membrane 4 being interposed between a surrounding environment 13 and the dispersion chamber 11 in which an at least partial vacuum was previously established.

The non-ordered movement of the sample of dry powder 5 is effected by a turbulent filling of the dispersion chamber 11 with ambient air 13 or any gas. This gas or the ambient air 13 is then used as a carrier of the material within the dispersion chamber 11.

This explosion and the filling of the dispersion chamber 11 with ambient air 13 or any gas gives rise to an unexpected phenomenon. The grains making up the sample of dry powder 5 have a tendency to push against one another and to form an homogeneous cloud of material within the dispersion chamber 11.

The sample of dry powder 5 is recovered for the purpose of analysis by a process of natural sedimentation of the grains in the dispersion chamber 11 on the surface to be treated 12.

In addition, when the surrounding pressure in the dispersion chamber is re-established owing to the rupture of the membrane 4, the butterflies prevent a lifting of the cylinder 10 and maintain the seal in order to prevent a loss of sample 4.

In order to use the device illustrated in FIG. 1, it is possible to proceed in the following manner. The surface to be treated 12 is disposed on the bottom base of the dispersion chamber 11, the dispersion chamber 11 is closed, by depositing the cylinder 10 on the bottom seal 7. The top cover 6 pivots on the right hand closure column 9 and will be placed in its compression position. The top and bottom seals 7 are compressed by butterfly screws (8) bolted onto the two lateral columns 9.

When the procedure for preparing the dispersion chamber 11 has ended, the membrane sample holder 3 is placed in the opening provided for this purpose on the top cover 6, and the membrane sample holder 3 is fixed by pressing on the fixing ring of the membrane sample holder 3.

The sample of dry powder 5 is disposed on the membrane 4 of the sample support previously fixed to the membrane sample holder 3.

A vacuum is produced in the dispersion chamber 11 by actuating the vacuum pump 1, which sucks out the air, the sample support membrane 4 will then tension; the pressure gauge 2 makes it possible to monitor the change in internal pressure in the dispersion chamber 11. When the pressure reaches the required level in the dispersion chamber 11 two cases may be envisaged:

Firstly, the sample support membrane 4 is intact and the explosion is effected by means of a punch 15 that perforates the sample support membrane 4, manually or automatically, thus initiating the explosion.

Secondly, the sample support membrane 4 can be sized so as to rupture automatically when the tension created by the difference in pressure existing between its two faces exceeds a given strength threshold of the membrane. This makes it possible to automate the procedure of exploding the sample support membrane 4.

The rupture of the sample support membrane 4 causes an opening in the dispersion chamber 11, which gives rise to an entry of ambient air 13 or of any gas or fluid sucked in by the vacuum previously prevailing inside the dispersion chamber.

The entry of the fluid in the dispersion chamber 11 is accompanied by a complete suction of the sample of dry powder 5 inside the dispersion chamber 11. Turbulence inherent in the filling process in the dispersion chamber 11 disperses the grains making up the sample of dry powder 5.

After a length of time sufficient to permit the natural sedimentation of the sample of dry powder 5 in the dispersion chamber 11, the treated surface 12, on which a uniform single layer of material has been deposited with an entirely random distribution of the particles, is removed.

Figure 2:
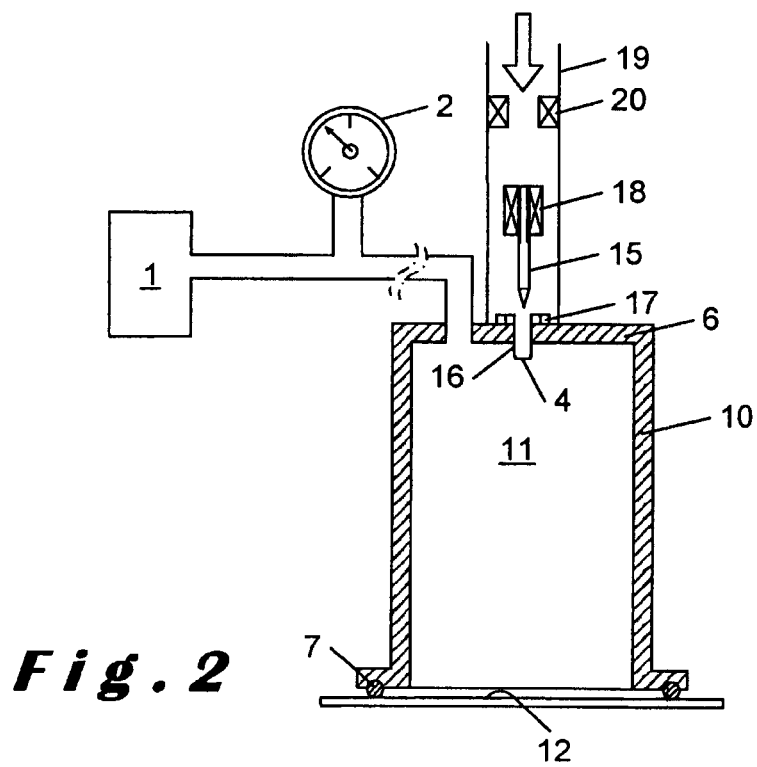
FIG. 2 is a schematic view of a variant embodiment of the device according to the invention.

The device according to FIG. 2 is differentiated from that in FIG. 1 by a simplification of the construction of the dispersion chamber 11, where the cylinder 10 and cover 6 are produced in one piece. The device also comprises a removable tubular capsule 16. This can be introduced into the top orifice of the dispersion chamber 11, in a sealed manner by virtue of its rim in the form of a collar 17 provided with a seal. The capsule is, at its top end, open to the surrounding environment. Its bottom end is provided with the membrane 4 that supports the sample to be dispersed. This bottom end projects inside the chamber.

This arrangement affords an easy placement of the sample in the capsule whilst the latter is not yet on the device. The capsule can easily be handled and replaced with another after dispersion of the sample that it contains. In addition, when the membrane ruptures the dispersion takes place at a distance from the cover 6, which assists total dispersion of the powder.

In the example embodiment according to FIG. 2, a punch has been shown, driven in movement in a linear motion towards and away from the membrane, in a motorised fashion. In the present case the punch is a solenoid rod driven by an electromagnet 18.

In the example illustrated in FIG. 2 a feed tube 19 is provided for the surrounding fluid around the orifice where the capsule 16 is housed. This tube is, at its top end, open towards the outside. It also contains, in its tubular cavity, gas ionisation means 20 known per se and depicted schematically, for example an electromagnetic coil. When the membrane 4 ruptures, there is a suction of gas from the outside, through the feed tube 19. This gas is then ionised by passing in front of the ionisation means 20. The effect of this ionisation is to promote further the mutual repulsion of the particles of powder and therefore to obtain an even better random dispersion of the powder on the surface to be treated 12.

Naturally the present invention is in no way limited to the embodiments described above and many modifications can be made thereto without departing from the scope of the accompanying claims.

The invention claimed is:

1. Method of dispersing a sample of dry powder on a surface in a dispersion chamber, comprising the steps of:

sealingly closing said dispersion chamber, placing the sample in means of introducing dry powder into the dispersion chamber, putting the chamber under negative pressure with respect to a surrounding environment, exploding a membrane that ruptures, this membrane serving as the above mentioned introduction means and being interposed between said surrounding environment and the interior of said dispersion chamber, the rupture of the membrane causing an opening in the dispersion chamber and an entry of a fluid composing the surrounding environment through the ruptured membrane, entrainment by this fluid of the dry powder placed on the membrane, inside the dispersion chamber in an evenly dispersed manner, and dispersing the dry powder on said surface, which is disposed on a bottom of the chamber and separate from the bottom of the chamber, said dispersion being carried out by separating and setting in movement of the sample of dry powder without producing an ordered movement of powder grains in the dispersion chamber; and analyzing the dry powder sample.

2. Method according to claim 1, characterised in that the putting under negative pressure comprises a gradual increase in pressure difference between the inside of the said dispersion chamber and the surrounding environment with tensioning of the said membrane and in that the explosion is caused by a rupture of the membrane due to a strength threshold thereof being exceeded.

3. Method according to claim 1, characterised in that the explosion is initiated by a perforation of the membrane.

4. Method according to claim 1, characterised in that it also comprises an ionisation of the said fluid making up the surrounding environment.

* * * * *